PLT-138 SR
CS203 OR PP 001018
BEST AVAILABLE COPY
June 19, 1951 E. S. BOERNER Plant Pat. 1,018
ROSE PLANT
Filed March 21, 1950
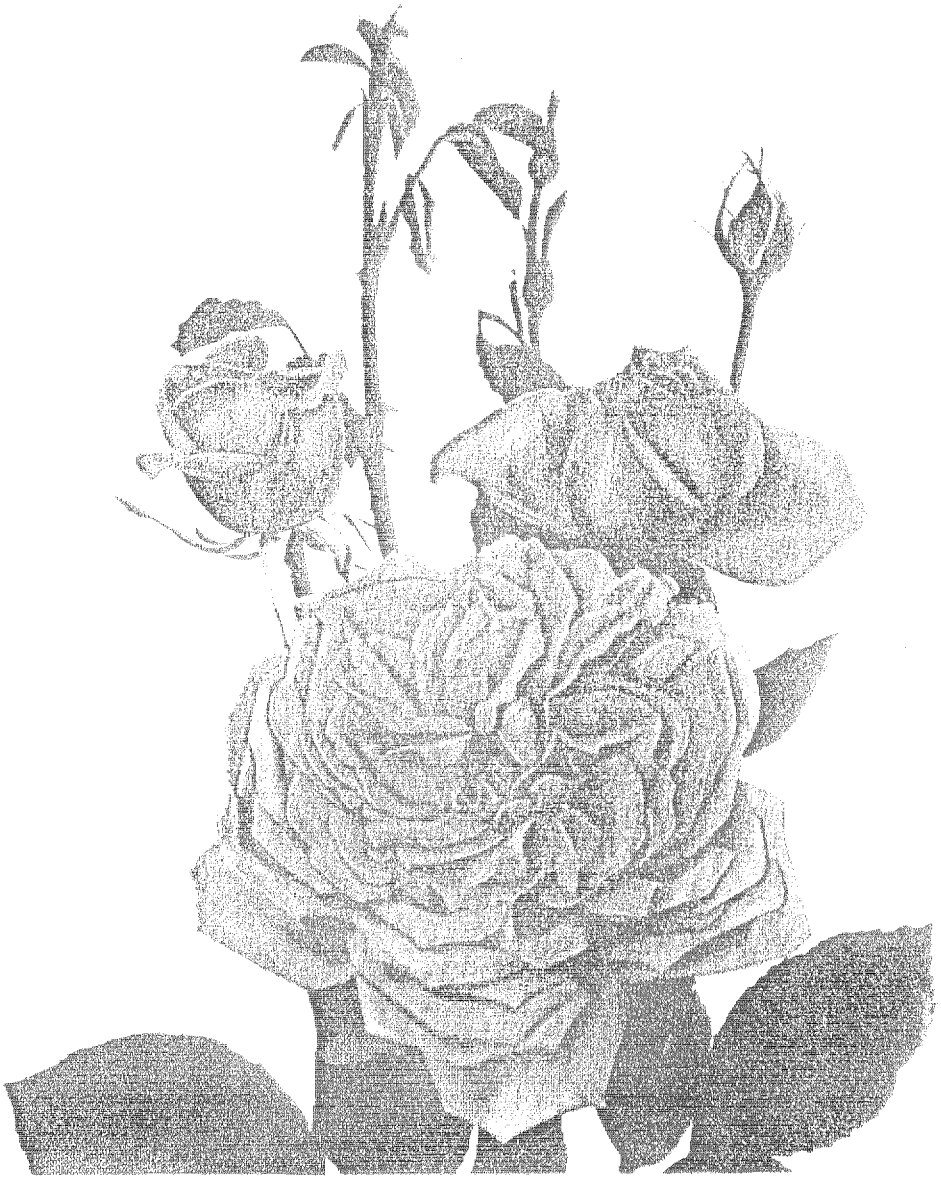
Inventor
E. S. Boerner
By Robert Odell
Attorney Patented June 19, 1951 Plant Pat. 1,018

UNITED STATES PATENT OFFICE 1,018

ROSE PLANT

Eugene S. Boerner, Newark, N. Y., assignor to Jackson & Perkins Company, Newark, N. Y., a corporation of New York Application March 21, 1950, Serial No. 150,984

1 Claim. (Cl. 47—61)

The present invention relates to a new and distinct variety of rose plant of the hybrid tea class, originated by crossing an unnamed hardy hybrid tea seedling, derived from a cross of another unnamed seedling ("Schoener's Nutkana" × an unknown seedling) × "Mrs. P. S. Du Pont," with the variety "Home Sweep Home," all of which varieties are unpatented.

The objective in making this cross was to obtain a rose having the general pink color characteristics of this new variety, but which was hardier, sturdier and more prolific than the parent variety "Home Sweet Home." This objective was achieved to a very marked extent by using a seedling which had some hardy and rugged species rose ancestry, and resulted in a new variety which bears flowers of Rose Pink color in all stages of bloom, which is vigorous and upright in growth, which is extremely prolific, with the buds and blooms produced singly and sometimes several on a stem, and which is endowed with superior hardiness inherited from its parent.

Asexual reproduction of this new variety by budding at Newark, New York, and at Pleasanton, California, shows that the foregoing characteristics come true to form and are established and transmitted through succeeding propagations.

In the accompanying drawing are shown specimens of the new variety, with the flowers in different stages of development from small bud to full-open bloom, and depicting the characteristic Rose Pink color thereof in all stages.

The following is a detailed description of the new variety, with color terminology in accordance with Ridgway's Color Standards and Nomenclature:

Parentage: Seedling.

*Seed parent.*—Seedling ("Schoener's Nutkana" × unknown seedling) × "Mrs. P. S. Du Pont."

*Pollen parent.*—"Home Sweet Home."

Classification: Botanic and commercial—hybrid tea.

*Flower*

(Observations made in greenhouse at Newark, New York, in the morning of December 30, 1949.)

Blooming habit: Recurrent—continuous.

Bud:

*Size.*—Large.

*Form.*—Globular. Is not affected by wet or hot weather.

Bud:

*Color.*—When sepals first divide—Pomegranate Purple, Plate 12. When petals begin to unfurl—Tyrian Rose, Plate 12. When half blown—inside of petals: Tyrian Rose, Plate 12, overcast with Rose Color, Plate 12; reverse of petals: Deep Rose Pink, Plate 12.

*Sepals.*—Branched. Curl back when petals begin to unfurl. Color—inside: Absinthe Green, Plate 31; outside: Light Bice Green, Plate 17.

*Calyx.* — Shape—pear. Size—small. Aspect—smooth. Odor when rubbed—none. Color—Lettuce Green, Plate 5.

*Peduncle.* — Length — medium. Aspect—smooth. Color—Parrot Green, Plate 6. Strength—erect; slender.

*Opening.*—Bud opens up well. Is not affected by adverse weather conditions.

Bloom:

*Size.*—Large. Average size when fully expanded—5 inches to 5½ inches.

*Borne.*—Singly and several together. Blooms very many on a plant.

*Stems.*—Medium length; normal strength.

*Form.*—When first open—cupped. Permanence—flattens.

*Petalage.*—Very double (many petals and stamens hidden). Number of petals under normal conditions—40.

*Color.*—Center of flower—between Deep Rose Pink, Plate 12, and Thulite Pink, Plate 26. Outer petals—Rose Pink, Plate 12. Base of petals (aiglet)—Amber Yellow, Plate 16. Inside of petals—Thulite Pink, Plate 26. General tonality from a distance—between Thulite Pink, Plate 26, and Rose Pink, Plate 12.

*Discoloration.*—General tonality at end of first day—between Deep Rose Pink, Plate 12, and Rose Pink, Plate 12. Second day—between Thulite Pink, Plate 26, and Rose Pink, Plate 12. Third day—Rose Pink, Plate 12.

Petals:

*Texture.*—Leathery. Is not affected by wet or hot weather.

*Appearance.* — Inside — satiny; outside — shiny.

*Form.*—Oval; notched.

*Arrangement.*—Informal (with "rags" in center). Petaloids in center—few; large.

*Persistence.*—Drop off cleanly.

*Fragrance.*—Slight. Nature—tea (average hybrid tea scent).

*Lasting quality.*—On the plant and as cut flower—long.

Genital organs:

*Stamens, anthers.*—Medium size; many. Color—Light Cadmium, Plate 4. Arrangement—mixed with petaloids.

*Stamens, filaments (threads).*—Medium length. Color—Pinard Yellow, Plate 4.

*Pollen.*—Color—Maize Yellow, Plate 4.

*Styles.*—Columnar; loosely separated, uneven length; medium length; thin.

*Stigmas.*—Color—Sea Foam Green, Plate 31.

*Ovaries.*—All enclosed in calyx.

*Plant*

Form: Bush.

Growth: Vigorous; upright.

Foliage: 3 to 5 leaflets.

*Size.*—Large.

*Quantity.*—Normal.

*Color.*—New foliage—upper side—Yellowish Oil Green, Plate 5; serrations—Oxblood Red, Plate 1. Under side—Oil Green, Plate 5; serrations—Oxblood Red, Plate 1. Old foliage—upper side—Varley's Green, Plate 18; under side—Bice Green, Plate 17.

*Shape.*—Oval pointed.

*Texture.*—Upper side and under side—smooth. Ribs and veins—ordinary.

*Edge.*—Serrated (saw toothed).

*Serration.*—Double; small.

*Leaf stem.*—Color—Rainette Green, Plate 31. Under side—prickles.

*Stipules.*—Medium length; smooth.

*Disease resistance.*—Resistant.

Wood:

*New wood.*—Color—Dull Citrine, Plate 16. Bark—smooth.

*Old wood.*—Color—Cress Green, Plate 31. Bark—smooth.

Thorns:

*Thorns.*—Quantity—on main stalks from base and on laterals from stalk—ordinary. Form—narrow; base; medium length; hooked downward. Color when young—Deep Vinaceous, Plate 27. Position—irregular.

*Prickles and hairs.*—None.

I claim:

A new and distinct variety of hybrid tea rose plant, characterized as to novelty by its vigorous, upright and sturdy habits of growth, by its superior hardiness, by its extremely prolific blooming habit, with the buds and flowers produced singly and sometimes several on a stem, and by the Rose Pink color of the flowers in all stages, substantially as shown and described.

EUGENE S. BOERNER.

No references cited.